United States Patent [19]

Bolanowski et al.

[11] 4,089,410

[45] May 16, 1978

[54] PACKAGE FOR FINE SUTURES, NON-NEEDLED, SINGLE OR DOUBLE ARMED

[75] Inventors: Lelia Ann Bolanowski, Hoffman Estates, Ill.; Alison Flatau, New Fairfield, Conn.

[73] Assignee: American Cyanamid Company, Stamford, Conn.

[21] Appl. No.: 831,030

[22] Filed: Sep. 6, 1977

[51] Int. Cl.² ............................................. A61L 17/02
[52] U.S. Cl. ............................ 206/63.3; 128/335.5; 206/459; 206/484; 229/87 R
[58] Field of Search .................. 128/335, 335.5, 339; 206/63.3, 227, 363, 370, 380, 388, 459, 484, 492; 229/87 R

[56] References Cited

U.S. PATENT DOCUMENTS

| | | | |
|---|---|---|---|
| 3,357,549 | 12/1967 | Staiti | 206/63.3 |
| 3,869,044 | 3/1975 | Olsson et al. | 206/63.3 |
| 3,876,068 | 4/1975 | Sonnino | 206/63.3 X |
| 3,939,969 | 2/1976 | Miller et al. | 206/484 X |

*Primary Examiner*—Steven E. Lipman
*Attorney, Agent, or Firm*—Charles F. Costello, Jr.

[57] ABSTRACT

A direct dispensing surgical suture label comprising a strand back panel, a strand cover and a strand cover side flap. The needled or non-needled ends of the surgical suture are held in a needle pocket. The needle pocket consists of a needle panel which is adjacent to the top portion of the strand panel and connected to it by a diagonal score line. The needle pocket also consists of needle panel side flaps each consisting of an upper rounded portion and a lower triangular portion. The upper portions are connected to the needle panel and the lower portions are connected to the strand panel by score lines. The needle pocket is protected by a needle cover consisting of an upper and a lower portion which folds over the strand cover and under the needle pocket respectively.

5 Claims, 11 Drawing Figures

PACKAGE FOR FINE SUTURES, NON-NEEDLED, SINGLE OR DOUBLE ARMED

BACKGROUND OF THE INVENTION

This invention relates to a surgical suture label which has a needle pocket, thus protecting the needles of an ophthalmic or other fine suture by confining them in the pocket until the pocket is opened. This invention also relates to a tearable suture envelope that can be torn from a tear notch across the face of the envelope so as to expose the above label.

Improved surgical techniques and, particularly, operative techniques under a microscope utilizing very fine structures on, for example, the hand, the eye, or the ear, have increased the demand for finer and finer sutures. In sewing together blood vessels and nerve sheaths of the hand, for example, sutures are desired which are smaller in diameter than a human hair. Sutures of such size are readily scored, abraded, or weakened by contact with the cut edge of a label during packaging.

From the standpoint of manufacture using common packaging machinery for other packages and having sutures in standard size packages for convenience in storage and inventory control, even the very fine sutures are most conveniently stored in the same size packages and envelopes as bigger sutures.

The requirements of uncompromised sterility are well known in the industry.

Applicants are not aware of any prior art references which, in their respective judgments as one skilled in the suture packaging art, would anticipate or render obvious the suture package of the instant invention. For the purpose of fully developing the background of the invention and establishing the state of the requisite art, however, the following references are set forth: U.S. Pat. No. 3,951,261, which discloses a dispensing device for micro-sutures comprising a separable needle mount and a flat card; U.S. Pat. No. 3,939,969 which discloses an inner suture retainer connected to an outer envelope so that when the envelope is opened, the suture end in the retainer is exposed; and U.S. Pat. No. 3,869,044 which discloses a reel-label on which are wound very fine surgical sutures.

This invention also has advantages over these prior art references. Because the present invention contains the suture ends in a needle pocket, the needles do not have to be mounted. Also, the pocket can contain non-needled suture ends which can be directly dispensed when the suture dispensing tab is pulled. By direct dispensing is meant that only the suture is removed from the sealed envelope, after the envelope is opened.

This package will present the needles of a fine suture in such a manner that they may be readily grasped and the suture dispensed directly from the package. The needle pocket of this package protects the needles of a fine suture by confining them in said pocket until package is opened and needles are presented for use. In addition the package insures that the fine suture is placed over only folded edges of paper. This eliminates suture damage by fraying caused when a fine suture is pulled over cut paper edges.

The needle pocket of the present invention does not open when the envelope is torn. That is, the sterile envelope can be opened without the suture end being disturbed. Because ophthalmic, plastic, etc., sutures can be smaller than the diameter of human hair, this reduces the risk that the suture end or needle will be hidden or drop into the label or between the label and the envelope prior to use.

The major advantages of the package of this invention are: (1) needle accessibility is greatly increased by insuring that the needles are confined to the needle pocket which is immediately visible when the envelope and dispensing tab are opened. (2) damage to the suture by fraying is prevented because the suture is not drawn over cut paper edges. (3) the suture is directly dispensed from the package. (4) the suture label is retained by the envelope, decreasing litter in the operating room. This package is useful in packaging a fine suture, non-needled or with one or two needles attached. The needle pocket in this package facilitates direct dispensing of the suture at the point of use.

SUMMARY OF THE INVENTION

A direct dispensing surgical suture label for fine sutures has now been invented. The label comprises a strand back panel. Connected to the back panel by a score line is a strand cover containing a diagonal cut on the top portion of the cover. The cut on the cover is on the opposite side of the back panel. Connected to the cover by a score line, and on the opposite side of the back panel is a strand cover side flap. The side flap contains a slit on the top portion of the score line. The top of the side flap is on a diagonal equal to the diagonal cut of the strand cover.

The needled or non-needled ends of the surgical suture are held in a needle pocket. The needle pocket consists of a needle panel which is adjacent to the top portion of the strand panel and connected to it by a diagonal score line. The needle pocket also consists of needle panel side flaps each consisting of an upper rounded portion and a lower triangular portion. The upper portions are connected to the needle panel and the lower portions are connected to the strand panel by score lines.

A needle cover consisting of an upper and a lower portion is adjacent to the top of said needle panel and is connected to it by a score line. The needle cover protects the needled or non-needled ends of the surgical suture in the needle pocket. A suture dispensing tab is adjacent the top portion of the upper needle cover and is connected to it by a score line. The strand cover is folded over the strand panel. A surgical suture strand is then contained between the back panel and the strand cover. The end of the surgical suture, either needled or non-needled, is then placed on the needle panel. The needle panel is folded under the back panel and the needle flaps are then folded under the needle panel. This creates the needle pocket. To cover the pocket, the lower needle cover is folded under the needle flaps and the upper needle cover is folded over the strand cover. The tab is folded over the upper cover. The strand cover side flap is then folded under the back panel. When the suture dispensing tab is pulled the ends of the surgical suture in the needle pocket are presented for direct dispensing.

The direct dispensing surgical suture label described above can have a heat sealable coating on one side. The label can be manufactured from stiff sterilizable stock.

The suture package of this invention consists of a sealed envelope having a tearing notch and a tear angle guideline. Enclosed in the suture package is the surgical suture label described above. The suture dispensing tab of the label is adjacent to the tear angle guideline of the envelope. When the envelope is opened, the tab is exposed.

A double envelope suture package comprising a strippable outer envelope containing the sealed envelope described above is also within the scope of this invention.

It can be seen that if a suture finer than a human hair is being used, great care in packaging and caring for the suture during manufacture, storage, and serving to the surgeon is required. Usually, sutures of such size are attached to an eyeless needle and are sold in short lengths, frequently with a needle on each end. For example, a standard size package contains a 7-0 chromic gut suture 12 inches long with two ⅜ inch circle lancet point needles, one on each end. The needles are very small and the workmanship of manufacture and handling is very delicate.

The present label is particularly adapted to sutures of size 6/0 and smaller, although it may, of course, be used with larger sutures if desired.

The label is formed from sheet label stock, one such being known as 90 pound, sterilizable, offset printing paper. Thinner paper could, of course, be used, but the standard 90 pound paper reduces the manufacturer's inventory problems and gives a label that is sufficiently stiff to be conveniently handled during manufacture, packaging and storage of the suture and provides a convenient carrier and holder up until the needle is gripped in needle forceps preparatory to surgical use. Without the present label which is particularly adapted for fine sutures both needled and non-needled sutures could be easily misplaced or lost because of their small size.

The suture array can be wound parallel or perpendicular to the length of the label. The form of array can be e.g., sinusoidal, helix, figure eight and the like.

The size of the needle side flaps confining the needle and suture can be varied as dictated by the needle size. Foam can also be used to further confine and protect the needles.

The present envelope can have size and type designations for the suture and needle printed on its external faces and it may be color coded to designate the type of suture and other useful information.

The present label is described in conjunction with drawings which illustrate the same.

DESCRIPTION OF THE INVENTION

Figure 1:
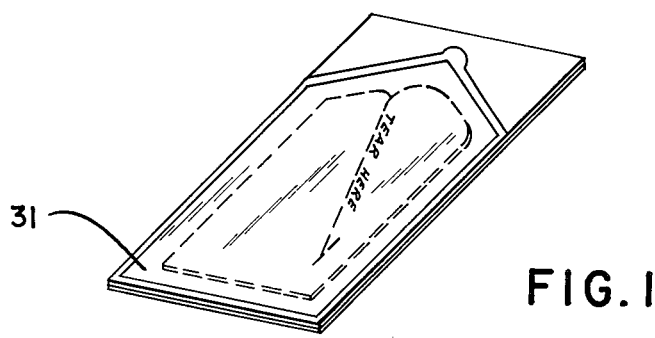
FIG. 1 shows a peelable outer envelope containing a tearable foil inner envelope.
Figure 2:
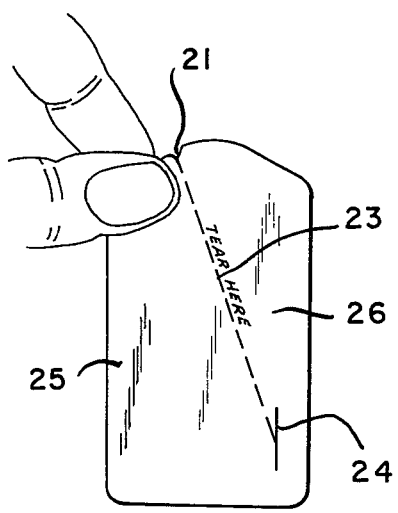
FIG. 2 shows the tearable inner envelope in position for use.

Referring to FIGS. 1 and 2, the outer envelope 31 is peeled off. Using the tearing notch 21 as a start the user can then open the inner envelope 25 by tearing the laminate longitudinally along the dotted guideline 23 to stop line 24 without detaching the torn portion 26. This action exposes the suture dispensing tab 20 shown in FIG. 3. To aid the user in proper use of the package a tear arrow could be indicated on the dotted guideline 23. FIG. 2 shows the inner envelope held in the position for use with the peelable outer envelope discarded.

Figure 3:
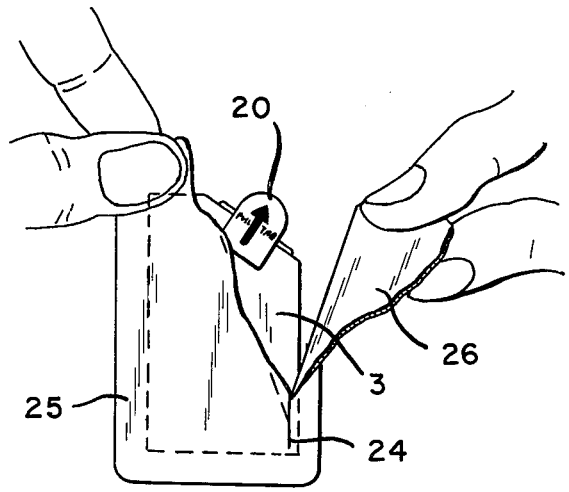
FIG. 3 shows the inner envelope being torn exposing the suture dispensing tab of the label.

FIG. 3 shows the availability of the suture dispensing tab 20 after the inner envelope 25 has been torn. The torn portion 26 is not detached from the inner envelope.

Figure 4:
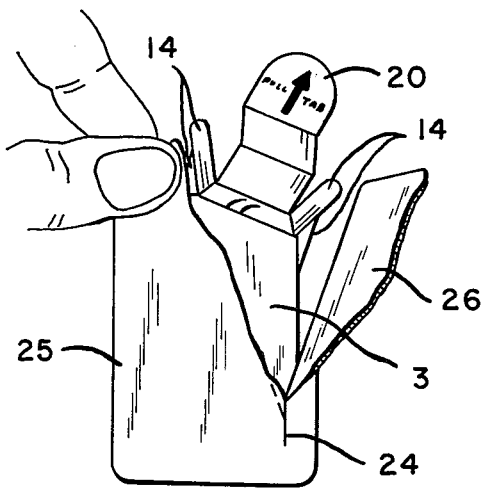
FIG. 4 shows the fully torn inner envelope and the fully opened label for direct dispensing.
Figure 5:
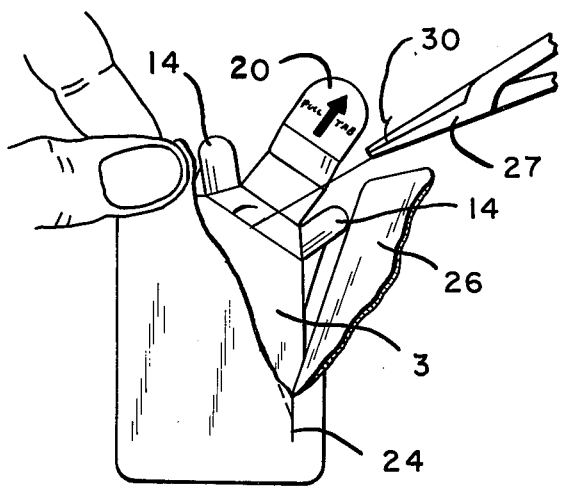
FIG. 5 describes one embodiment of the use of the direct dispensing package by removing the needles with needle holders.

FIGS. 4 and 5 show the suture dispensing tab 20 pulled and the needle 30 being grasped by the needle holders 27. FIGS. 4 and 5 also show part of the strand cover 1. Due to the design characteristics of the suture label in general and the strand cover in particular, the label is securely locked within the opened portion of the envelope 25 and the entire package remains intact. Thus no additional materials or articles other than the needle and strand are added to the operating area. Related hazards are thus minimized and accountability is simplified.

Figure 6:
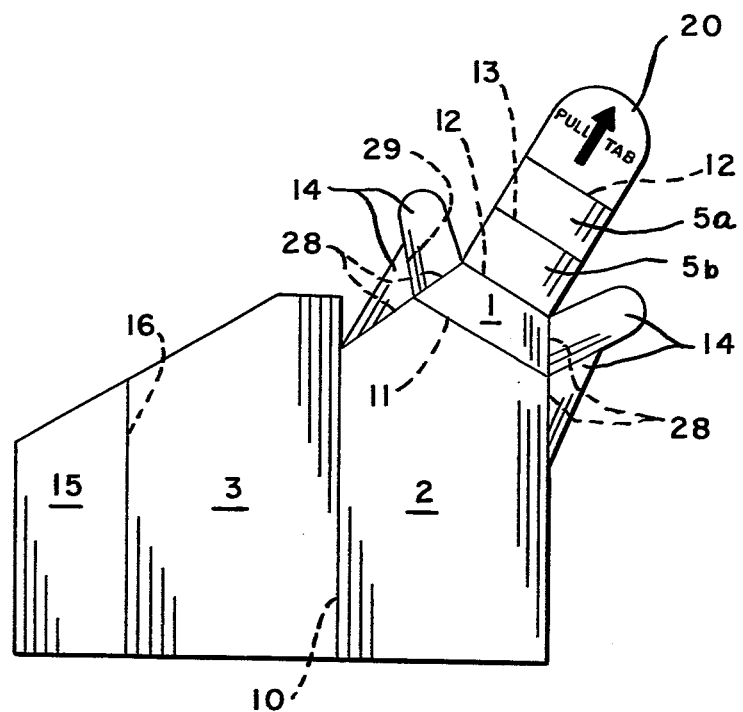
FIG. 6 is a front view of the suture label.

FIG. 6 shows a suture label cutout and scored from a sheet of sterilizable paper which can be coated with polyethylene for heat sealing. As shown in FIG. 6, the suture cover consists of a back panel 2 to which is attached respectively, by score lines 10, 11, a strand cover 3 and a needle panel 1. Needle side flaps 14 are attached by score lines 28 to needle panel 1 and to back panel 2. Score line 27 separates the needle side flap into two parts which is important to the formation of the needle pocket. The suture dispensing tab 20 is separated from the needle panel 1 by an upper and lower needle cover 5a and 5b. The suture tab, needle covers and the needle panel are attached to each other by score lines 12 and 13. Strand cover side flap 15 is attached to the strand cover 3 by score line 16.

Figure 7:
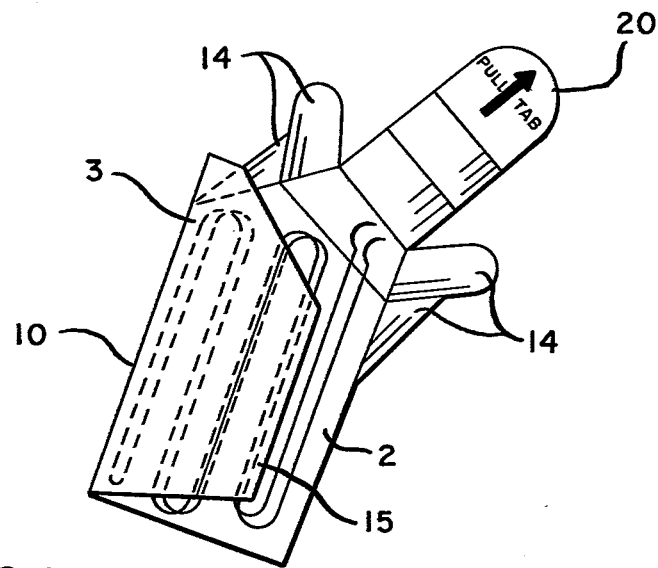
FIG. 7 shows the strand cover partially folded over the back panel of FIG. 6.

FIG. 7 shows the preferred folding of the strand cover flap 3 over the back panel 2 along the score line 10.

The strand configuration must allow for the strand to be dispensed without tangling. In the preferred embodiment, shown in FIG. 7, the configuration is sinusoidal. However, any particular series of loops or coils that allow the strand to dispense freely without tangling can be used. The relationship of the needled end of the strand to the rest of the coil is of no major significance as long as the configuration of the strand allows it to be directly dispensed.

Figure 8A:
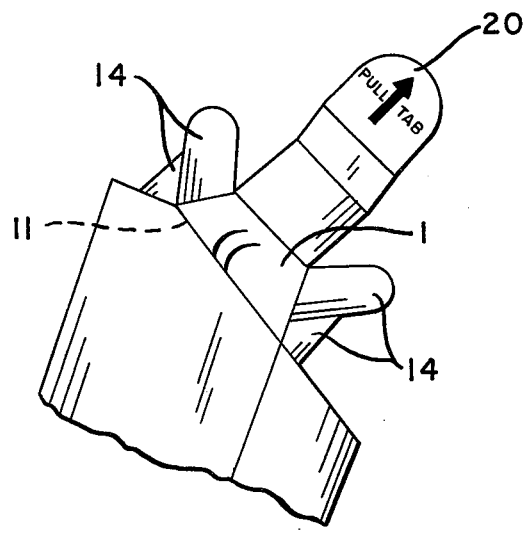
FIGS. 8a–8c describes the formation of the suture end pocket by folding the needle front panel and the needle side flap.
Figure 8B:
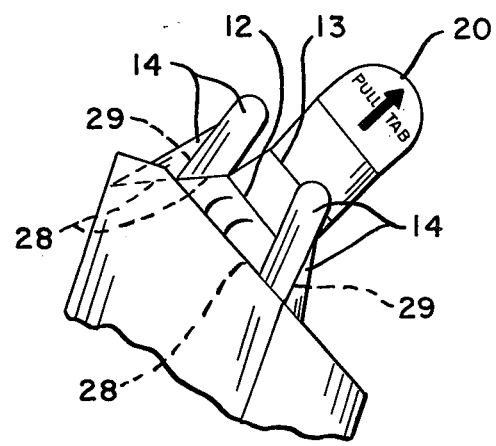
Figure 8C:
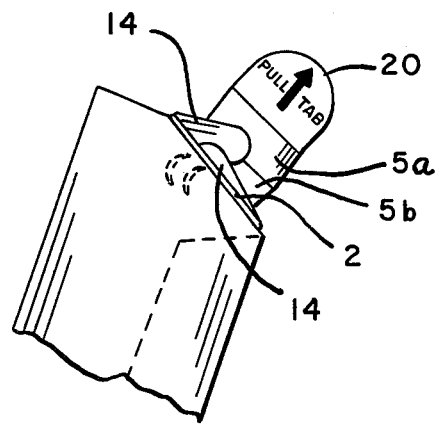

FIGS. 8a–8c teach the proper folding of the needle panel 1 and the needle side flaps 14 to create the needle pocket. Referring to FIG. 8a, the needle panel 1 is folded to the rear along score line 11. Because of the score lines 28 and 29 this will cause the needle side flaps 14 to approximately face each other. In FIGS. 8b and 8c, as the needle panel is folded completely under the strand back panel 2, the rounded portions of the needle side flaps 14 fold onto each other. A needle pocket is thus formed between the needle panel and the rounded portions of the needle flaps. The needle cover 5a and 5b folds under and over, respectively, the needle pocket along score lines 12 and 13.

Figure 9:
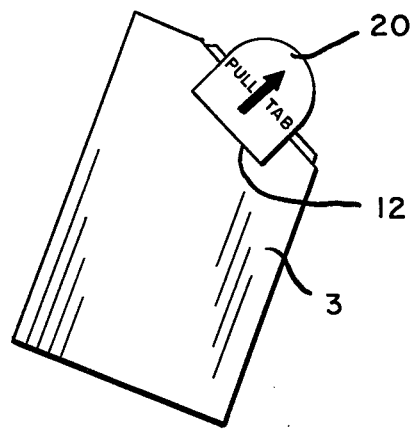
FIG. 9 describes the lower and upper needle cover folded under and over, respectively, the needle pocket of FIG. 8c.

FIG. 9 shows the relationship of the suture dispensing tab 20 to the strand cover 3. The suture dispensing tab 20 is folded over the upper needle cover 5b, along score line 12.

We claim:

1. A direct dispensing surgical suture label comprising a strand back panel;

a strand cover containing a score line and a diagonal cut on the top portion of said cover opposite said panel;

a strand cover side flap containing a score line, and a slit on the top portion of said score line, the top of said flap aligned with the diagonal cut of said cover;

a needle pocket consisting of a needle panel adjacent and on a diagonal to the top portion of said strand panel and connected by a diagonal score line, and two needle panel side flaps on opposite sides of said needle panel each consisting of an upper rounded portion and a lower triangular portion, said upper portion connected to said needle panel and said lower portion connected to said strand panel by score lines;

a needle cover consisting of an upper and lower portion adjacent to the top of said needle panel;

a suture dispensing tab adjacent the top portion of said upper needle cover;

whereby when said strand cover is folded over said strand panel and a surgical strand is contained between said strand panel and said strand cover with the ends of said surgical suture placed on said needle panel and said needle panel is folded under said strand panel and said needle flaps are folded under said needle panel and said lower needle cover is folded under said needle flaps and said upper needle cover is folded over said strand cover and the tab folded over said upper cover and said strand cover side flap is folded under said strand panel such that when the suture dispensing tab is pulled the ends of said surgical suture in said needle pocket is presented for direct dispensing.

2. A direct dispensing surgical suture label described in claim 1 having a heat sealable coating on one side.

3. A direct dispensing surgical suture label described in claim 1 manufactured from stiff sterilizable stock.

4. A suture package consisting of a sealed envelope having a tearing notch and a tear angle guideline and enclosed therein a direct dispensing surgical suture label as set forth in claim 1, and in which said suture dispensing tab is adjacent to the tear angle guideline of said envelope, such that when said envelope is opened, said tab is exposed.

5. A double envelope suture package comprising a strippable outer envelope containing a sealed envelope described in claim 4.

* * * * *